US012575771B2

(12) United States Patent
Lykke et al.

(10) Patent No.: US 12,575,771 B2
(45) Date of Patent: Mar. 17, 2026

(54) SYRINGE FOR OBTAINING A TARGET VOLUME OF BLOOD

(71) Applicant: RADIOMETER MEDICAL APS, Brønshøj (DK)

(72) Inventors: Jacob Lykke, Brønshøj (DK); Louise Wagner Nørgaard, Brønshøj (DK)

(73) Assignee: RADIOMETER MEDICAL ApS, Brønshøj (DK)

( * ) Notice: Subject to any disclaimer, the term of this patent is extended or adjusted under 35 U.S.C. 154(b) by 929 days.

(21) Appl. No.: 17/756,825

(22) PCT Filed: Dec. 16, 2020

(86) PCT No.: PCT/EP2020/086388
§ 371 (c)(1),
(2) Date: Jun. 3, 2022

(87) PCT Pub. No.: WO2021/122721
PCT Pub. Date: Jun. 24, 2021

(65) Prior Publication Data
US 2023/0008783 A1 Jan. 12, 2023

(30) Foreign Application Priority Data
Dec. 18, 2019 (DK) .............................. PA201901495

(51) Int. Cl.
*A61B 5/15* (2006.01)

(52) U.S. Cl.
CPC .... *A61B 5/15003* (2013.01); *A61B 5/150213* (2013.01); *A61B 5/150351* (2013.01)

(58) Field of Classification Search
CPC .......... A61B 5/15003; A61B 5/150213; A61B 5/150351; A61B 5/150221;
(Continued)

(56) References Cited

U.S. PATENT DOCUMENTS 4,267,846 A * 5/1981 Kontos .................. A61B 5/153
604/220
4,373,535 A 2/1983 Martell
(Continued)

FOREIGN PATENT DOCUMENTS

EP 0 102 070 A2 3/1984
EP 0 102 073 A2 3/1984
(Continued)

OTHER PUBLICATIONS

International Search Report of International Application No. PCT/EP2020/086388, dated Apr. 16, 2021 (three pages).
(Continued)

*Primary Examiner* — James D Ponton
*Assistant Examiner* — John A Doubrava
(74) *Attorney, Agent, or Firm* — FBT Gibbons LLP

(57) ABSTRACT

A syringe for obtaining a target volume of blood is presented. The syringe (1) comprises a barrel (2), wherein a plunger (4) is arranged within the barrel (2) to be displaceable along a displacement direction (X). Furthermore the barrel (2) and the plunger (4) together provide for a first stop (20) and second stop (22), wherein the first stop (20) is configured for positioning a filter (100) at a predetermined location along the displacement direction (X) thereby defining a target volume of blood and a buffer volume. Moreover, the second stop (22) is configured to stop the plunger (4) from expelling more than the buffer volume from the syringe (1) for obtaining the target volume of blood when the plunger (4) is pushed towards the distal end (30) of the syringe (1) along the displacement direction (X). In addition, the syringe (1) facilitates that the syringe (1) fills itself with the target volume of blood by a self-filling procedure using blood that is under pressure, like arterial blood, and using the filter (100) located in the plunger (4).

20 Claims, 3 Drawing Sheets

(58) Field of Classification Search
CPC ........ A61B 5/150244; A61B 5/150992; A61B
5/153; A61M 2005/3114; A61M 5/3129;
A61M 5/31501
See application file for complete search history.

(56) References Cited

U.S. PATENT DOCUMENTS

| | | | |
|---|---|---|---|
| 4,448,206 A | | 5/1984 | Martell |
| 4,572,210 A | | 2/1986 | McKinnon |
| 4,572,569 A | | 2/1986 | HaBmann |
| 4,660,569 A | * | 4/1987 | Etherington ..... A61B 5/150244 604/190 |
| 5,125,415 A | * | 6/1992 | Bell ................. A61B 5/150213 604/199 |
| 2019/0365565 A1 | * | 12/2019 | Bryant .................... A61P 27/02 |
| 2021/0077738 A1 | * | 3/2021 | Dadachanji ....... A61M 5/31513 |

FOREIGN PATENT DOCUMENTS

| | | |
|---|---|---|
| EP | 1 529 489 A1 | 5/2005 |
| SE | 308 002 B | 1/1969 |
| WO | WO 83/03173 | 9/1983 |

OTHER PUBLICATIONS

Written Opinion of the International Search Authority for International Application No. PCT/EP2020/0861388 (six pages).

* cited by examiner

S1          S2          S3          S4

S1        S2        S3        S4        S5

SYRINGE FOR OBTAINING A TARGET VOLUME OF BLOOD

This application is a national stage filing under 35 U.S.C. § 371 of International Application No. PCT/EP2020/086388, filed on Dec. 16, 2020, which claims priority to Danish Patent Application No. PA201901495, filed on Dec. 18, 2019. The contents of these applications are each incorporated herein by reference.

FIELD OF THE INVENTION

The present invention relates to syringes. In particular, the present invention relates to a syringe for obtaining a target volume of blood from a patient and for easily ventilating the sample, i.e. the obtained target volume of blood, with only a short push on the plunger, and the invention relates to a method of filling a syringe with a target volume of blood and for easily ventilating the sample, as well as to a package comprising a syringe. Such a syringe may include a mechanism to obtain a target amount of blood, in particular a volume sufficient for a blood gas test.

BACKGROUND OF THE INVENTION

Patient blood management focuses on improved patient care by managing the handling of blood, including the rational use of blood during patient care and evaluation. However, for most users of syringes, the obtaining of blood for a sample is a trivial task and only small blood volumes are required and therefore the volume of the blood sample is not a priority for the user, although it is a task which can be performed as often as every hour on some patients. Especially for blood gas tests, the amount of blood needed is very little, so that a user needs to handle the syringe very carefully. The inventors of the present invention identified the need to provide for an accurate blood obtainment with a syringe.

SUMMARY OF THE INVENTION

The object of the present invention may be seen in providing an improved syringe, and in particular, in improving the ergonomics of withdrawing blood and to increase the security of the syringe's handling.

The problem is solved by a syringe according to claim 1. Further embodiments and ad-vantages of the present invention are incorporated in the dependent claims and the description.

Technical terms are used by their common sense. If a specific meaning is conveyed to certain terms, definitions of terms will be given in the following in the context of which the terms are used.

According to a first aspect of the present invention, a syringe for obtaining a target volume of blood is presented. The syringe comprises a barrel, wherein a plunger is arranged within the barrel to be displaced along a displacement direction, and wherein the barrel and the plunger together provide for a first stop and a second stop. The first stop is configured for positioning the filter at a predetermined location along the displacement direction thereby defining a target volume of blood and a buffer volume of blood. The second stop is configured to stop the plunger from expelling more than the buffer volume for obtaining the target volume of blood when the plunger is pushed towards a distal end of the syringe along the displacement direction. Moreover, the plunger comprises a filter, wherein the filter is configured to be gas-permeable when the filter is not in contact with blood, and the filter is configured to become gas- and fluid-impermeable when getting in contact with blood. Moreover, the plunger is fluid-sealing when the filter is gas-impermeable, and the plunger is configured for guiding air out of the barrel and through the filter towards outside the syringe during a self-filling process of the syringe until the blood comes into contact with the filter which then changes to become both gas- and liquid-impermeable.

The advantageous use of such a syringe will be shortly summarized in the following. When the self-filling process starts, the plunger of the syringe has preferably been set by the user to the first stop, where the target volume of blood including a buffer volume of blood will be obtained. The incoming blood is pushed into the compartment, which results from the combination of the plunger with the barrel, until the compartment is filled, since at this point in time the blood get into contact with the filter which then changes its gas- and liquid-permeability and hence now blocks gas from passing through the filter. No gas can leave or enter the syringe anymore through the plunger and its filter. The user may then release the syringe from being attached to a blood vessel of the patient and may close/seal the tip of the syringe with e.g. a cap or a ventilation tip cap. Such ventilation tip caps are known to the skilled person, and are exemplarily described in Applicant's European patent application EP 1 549 385. Thus, in a preferred embodiment the syringe comprises a ventilation tip cap. When sealing the tip with e.g. a ventilation tip cap also no air can get into the syringe from the tip.

However, the syringe of the present invention allows for an easy ventilation of the sample, with only a short push on the plunger. This push moves the plunger from the first stop to the second stop and the buffer volume of blood, and any air present in the barrel after releasing the syringe from being attached to a blood vessel, is pushed out of the barrel and into to ventilation cap. In particular, the buffer volume can comprise blood, air or any other fluid. The size of the buffer volume is selected such that the target volume of blood is likely to be in the syringe after the buffer volume is removed from the syringe through a ventilation tip cap of the syringe. In this way, "loose" air that is still in the syringe after the self-filling process has been completed can be pushed out via the tip of the syringe. If a ventilation tip cap is mounted on the tip, then said loose air can be pressed by the user with the plunger through the ventilation cap. Since the movement of the plunger is then blocked by the second stop, the location of this stop can be used to define the volume of the blood that is contained within the compartment. Thus, the first stop sets the volume before venting and the second stop sets the volume after venting, i.e. the target volume of blood.

In other words, the plunger is used for obtaining the target volume together with the filter at the first stop, i.e. the stop closer to the distal end 30 of the syringe (see FIG. 1). The plunger is used for venting the syringe such that the whole syringe from the filter to the tip of the syringe is filled with blood. This is performed because you need to get any "loose" air in the blood volume out of the syringe before transport and subsequent analysis. The tip of the syringe is sealed by a cap or preferably by a ventilated tip cap that can guide the air out. This will be elucidated and explained in the context of embodiments of the present invention hereinafter.

In general, the movement or the displacement between the barrel and the plunger is interrupted by a first and/or a second stop. The first stop limits the displacement between the plunger and the barrel so that a volume within the syringe occurs such that a target volume of blood (including a buffer volume of blood) can be pressed in the syringe. This is illustrated with reference to the FIG. 1 and its description hereinafter. The syringe of the present invention provides the specific advantage that only the required amount of blood is extracted from a patient. Therefore, no unnecessary stress occurs for the patient by only extracting the required amount of blood. Additionally, the first stop may be set to define a target volume of blood (including a buffer volume of blood), which is sufficient to perform a blood gas test with the target blood volume. Preferably, the target volume of blood, and thereby the position of the first stop, can be defined in dependency on a specific blood gas test. Furthermore, the movement and/or the displacement between the plunger and the barrel can be interrupted by the second stop, which is in particular configured to stop the plunger from expelling blood when pushed in the displacement direction, which is also illustrated with reference to the FIG. 1 and its description. The first stop and the second stop are understood as elements providing a stopping function of the plunger along the displacement direction, as will be explained in more detail hereinafter in the context of particular embodiments.

As will become apparent from and elucidated with the following explanations, the syringe of the present invention facilitates that the syringe fills itself with the target volume of blood and the buffer volume of blood by a self-filling procedure using blood that is under pressure, like arterial blood, and using a filter that is located at or in the plunger. Moreover, the present invention facilitates an easy ventilation of the sample, i.e. the obtained target volume of blood, with only a short push on the plunger. This will be described in more detail hereinafter.

In detail, the plunger comprises, has and/or incorporates a filter, i.e. a filter element and/or a component, which has a filtration and/or blocking functionality. The filter has the functionality that it changes its gas permeability, particularly its permeability to air, depending on whether the filter is in mechanical contact with blood. In other words, the filter is gas-permeable, when the filter is not in contact with blood, i.e. before using the syringe of the present invention and the filter becomes gas-impermeable, preferably air impermeable when the filter gets into contact with the patient's blood during the use of the syringe by the user. Therefore, placing the filter at a position chosen by the manufacturer/user of the syringe, allows obtaining a desired target volume of blood even during a self-filling process of the syringe as described herein.

The term "filter" shall be construed broadly in the context of the present invention, such that any component that is configured to let gas, preferably air, through, i.e. being gas permeable, when not being in contact with blood and that is configured to stop gases, i.e. becomes gas impermeable, when being brought into contact with blood, shall qualify for the filter of the syringe of the present invention.

The plunger is fluid-sealing when the filter is gas-impermeable. In other words when the filter is in its gas-impermeable state then the plunger seals fluid tightly, preferably blood tightly, the barrel/closed volume of the barrel from the rest of the syringe, which extends from the barrel towards the opening of the syringe, in which the plunger is introduced. This can clearly be gathered from e.g. the embodiments of FIGS. 1 and 2.

Moreover, the plunger is configured for guiding air out of the barrel and through the filter towards outside the syringe during a self-filling process of the syringe. Thus, the plunger provides for a fluid connection in this state between the barrel and the filter, as well as between the filter and the outside, i.e. the surrounding atmosphere, of the syringe. In this state air can flow from the barrel through the plunger, through the filter and is then guided by the channel outside of the syringe. An air channel inside the plunger may be an exemplary mechanical structure for this functionality, as exemplarily depicted in the embodiments of FIGS. 1 and 2.

In other words, the syringe is a self-filling syringe, which can be used for obtaining blood from a patient. Therefore, the syringe is attachable to arterial vessels of a patient. The blood in arterial vessels is under pressure; therefore, it is sufficient to only attach the syringe to the patient and not necessarily actively drawing blood from the patient with negative pressure. During such a process of a self-filling of a syringe, the plunger allows/facilitates a transport of air from the barrel of the syringe through the plunger and the filter of the plunger out of the syringe. Since blood is entering the barrel of the syringe in such a process, the air that was previously residing in said part of the barrel has to be transported out of the syringe. The plunger of the syringe of the present invention provides this functionality by e.g. a channel and the filter. This functionality will be explained in more detail hereinafter and can be gathered e.g. from the embodiments of FIGS. 1 and 2.

Thus, such a syringe is configured to be automatically filled with a predefined volume of blood (i.e. the target volume of blood including a buffer volume of blood) without the need that the user pulls or withdraws the plunger back. Thus, using this syringe in a self-filling procedure, will result in a blocking a further inflow of blood into the syringe, when the desired volume is reached, since at this point in time the filter in or at the plunger becomes impermeable for gas/air/fluid and hence no further blood may enter the barrel.

The first stop, the second stop and the filter are chosen/positioned at the syringe in such a way that when the plunger reaches the first stop during a self-filling process of the syringe, the filter target volume of blood has already been received by the barrel of the syringe and the filter is in contact with blood. In such a way it is ensured that the filter changes its fluid permeability at the time/state when the target volume of blood has been received. No further air/blood can pass the filter and the received blood can be safely kept after venting when provided with a cap on it in the syringe after removing the syringe from e.g. an arterial vessel of a patient.

In addition, the filter is configured for changing, altering and/or adapting the plunger to be gas-permeable, open and/or permeable to air, when the filter is not in contact with blood, i.e. in its initial state or condition, how it is sold to the user. Furthermore, the filter is configured for changing, altering and/or adapting the plunger to be fluid-sealing when the filter has been brought into contact with blood, and as a consequence has closed down its permeability for fluids and gases, preferably at least for air. Thus, in a way the plunger is configured for providing and/or establishing a self-filling effect of the syringe, when the plunger is gas-permeable. When blood that is under pressure, like arterial blood, is brought in contact with the distal opening of the syringe then blood is transported into the barrel of the syringe. Furthermore, the filter is configured for sealing the barrel respectively preventing blood passing the filter, when the filter is fluid-sealing, i.e. when the filter of the syringe/plunger is in contact with blood and thus is not permeable for blood and/or air.

As has been described before, the syringe can be seen as a self-filling syringe, which can be used for obtaining blood from a patient. Therefore, the syringe is attachable to arterial vessels of a patient. The blood in arterial vessels is under pressure; therefore, it is sufficient to only attach the syringe to the patient and not necessarily drawing blood from the patient with negative pressure by e.g. the user. The pressurized blood flows into the barrel such that the air inside the barrel needs an outlet. In case the syringe is removed from the arterial vessel the plunger needs to be sealed otherwise the blood would flow out of the syringe. Therefore, the filter as described before is positioned at and/or inside the plunger. The filter is permeable to air as long as the filter is not in contact with blood, thereby providing an outlet for the air and allowing that blood can be pressed into the barrel. However, when removing the syringe from the arterial vessel the plunger needs to be sealed such that the accommodated blood in the barrel cannot leave the barrel. In order to seal the barrel with the plunger, the filter becomes gas tight when the targeted volume of blood is in the barrel. The plunger and thereby the filter can be positioned with the help of the first and second stop such that only the required amount of blood is obtained. This increases not only the safety and reliability of blood removal procedures at the point of care, but also allows an easy handling of the syringe during blood removal and a safe and easy transport into particularly pneumatic post systems. This can be done after the sample has been vented properly and when the syringe is provided with a cap on the tip.

The barrel as described herein may preferably be an extruded or injection molded body made of plastic or a plastic composite, which has a mainly circular cross-section. Within the barrel, a plunger is located which may be also preferably made from a plastic or plastic compound. One part of the plunger is configured to be manipulated by a user of the syringe. On the other end of the plunger, a rubber may be foreseen, which is configured to generate a fluid- and/or gas-tight seal between the plunger and the barrel. Furthermore, the plunger is positioned within the barrel so that the plunger can be moved along the extrusion of the barrel. The plunger is moved within the barrel along a displacement direction, which is defined by the geometry of the barrel.

According to an exemplary embodiment of the present invention, the plunger comprises a channel and the filter is positioned at least partially inside the channel. The channel is configured for guiding the air out of the barrel and through the filter towards the outside of the syringe during the self-filling process of the syringe.

In other words, the channel provides a gas connection between the barrel and the filter, as well as between the filter and the outside, i.e. the surrounding atmosphere, of the syringe. Air can flow from the barrel through the channel, through the filter and is then guided by the channel outside of the syringe. A detailed embodiment of such a plunger is shown in FIGS. 1 and 2.

According to an exemplary embodiment of the present invention, the barrel comprises a proximal end at which a first opening for introducing the plunger into the barrel is located, and the barrel comprises a distal end at which a second opening for receiving the target volume of blood is located. Moreover, the second stop is located closer to the first opening than the first stop.

According to an exemplary embodiment of the present invention, the channel has a first aperture at a proximal end of the plunger, and the channel has a second aperture at a distal end of the plunger. The filter is located at least partially inside the channel and in-between the first aperture and the second aperture of the channel.

According to a further exemplary embodiment, the filter is configured for ventilating gas through the channel of the plunger, when the filter is gas-permeable (i.e. when it is not in contact with blood), and the filter is configured for sealing the channel of the plunger fluid-tightly, i.e. gas and fluid-tightly when the filter is gas-impermeable.

In other words, the plunger fluid tightly seals, e.g. with a piston comprising a sealing element, the barrel at the inner surfaces of the barrel, as it is depicted in e.g. FIG. 1. However, in the sections of the plunger where the channel and filter are located (see e.g. FIGS. 1 and 2), the sealing functionality of the plunger depends on whether the filter is in contact with blood or not. In case the syringe is currently filled with blood but the filter is not yet in contact with blood, only air is ventilated/guided through the filter and the filter has and keeps its functionality to allow air to pass through. However, when blood reaches the filter, the filter changes its permeability and blocks any further gas/air/fluid movement through the filter. Hence, due to the position of the filter relative to the rest of the syringe, the target volume of blood (including the buffer volume of blood) can be obtained without user intervention for the process of stopping the blood flow into the syringe. Since now the plunger blocks fluid/blood movement out of the barrel also in the sections of the plunger where the filter and the channel are located (because the filter does not allow blood to pass through), the plunger is in this situation entirely fluid tightly sealing the barrel. Thus, the filter is configured for sealing the channel of the plunger fluid-tightly, when the filter is gas-impermeable.

According to an exemplary embodiment of the present invention, the first stop is configured for positioning the filter at a predetermined location along the displacement direction to define the target volume of blood including a buffer volume.

As has been described hereinbefore, due to the position of the filter relative to the rest of the syringe, the target volume of blood desired by the user/manufacturer can be obtained without user intervention for the process of stopping the blood flow into the syringe. The blood flow into the syringe automatically stops when the filter changes its permeability.

According to an exemplary embodiment of the present invention, the syringe comprises a ventilation tip cap on the tip of the syringe. The ventilation tip cap is configured for preventing air from moving through the tip into the syringe, and the ventilation tip cap is configured for allowing air to be pushed from inside the syringe, particularly the barrel, out of the syringe through the ventilation tip cap when the plunger is moved from the first stop to the second stop.

According to an exemplary embodiment of the present invention, the barrel comprises a proximal end at which a first opening for introducing the plunger into the barrel is located. The barrel comprises a distal end at which a second opening for drawing the target volume of blood into the syringe is located. Additionally, the second stop is located closer to the first opening than the first stop.

The first opening is preferably located on one side of the barrel wherein the diameter of the first opening is preferably the same as the whole barrel. Thereby, the plunger can be inserted more easily into the barrel, which is advantageous for the assembly of the barrel with the plunger. Furthermore, the barrel comprises preferably a distal end at which a second opening is located, wherein the second opening preferably has a diameter smaller than the diameter of the barrel. At the second opening, blood can flow into the barrel. For example, an access could have been inserted to the patient and the second opening can be attached to the access and thereby blood can be obtained from the patient. Furthermore, the second stop is located closer to the first opening than the first stop. With this configuration, it is assured that only the required amount of blood is obtained from the patient because the filter is positioned dependent on the location of the first stop. This aspect can easily be gathered from FIG. 1 and the corresponding description. Furthermore, the target volume of blood is obtained by the second stop, after the plunger has been pushed from the first stop to the second stop and thereby expelling the buffer volume of blood and the air that might be present inside the barrel before ventilation of the sample.

According to another exemplary embodiment of the present invention, the plunger comprises a channel. The channel has a first aperture directed to the first opening of the barrel. The channel has a second aperture directed to the second opening of the barrel. The filter is located at least partially inside the channel and in-between the first aperture and the second aperture. The filter is configured for ventilating fluid through the channel of the plunger, when the filter is in the first condition. The filter is configured for sealing the channel of the plunger fluid-tight, when the filter is in the second condition.

In other words, the plunger comprises, has and/or forms a channel, conduit and/or canal. The channel has, comprises and/or forms a first aperture respectively opening directed to and/or located towards the first opening of the barrel. In addition, the channel has, comprises and/or forms a second aperture and/or opening directed to and/or located towards the second opening of the barrel. Furthermore, the filter is located and/or orientated at least partially inside and/or within the channel and in-between the first aperture and the second aperture. The filter can comprise a first side facing the first aperture and a second side facing the second aperture, wherein the filter is configured for being able to block any fluid between the first and second side of the filter, when the filter is in contact with blood and/or is soaked with blood. Additionally, the filter is configured for ventilating respectively letting through air, through the channel of the plunger when the filter is gas-permeable. Furthermore, the filter is configured for sealing and/or locking the channel of the plunger fluid-tight respectively impermeable, when the filter is in the second condition, i.e. when the filter is gas-impermeable.

In an exemplary embodiment, the plunger comprises a channel, which extends through the plunger, in particular along the displacement direction. The channel ventilates air out of the volume formed by the plunger within the barrel in case the syringe is attached to arterial vessels and blood is pressed into the syringe. As soon as the barrel is filled with the targeted blood amount, the filter is positioned in the barrel such that the filter is fully covered and/or soaked with blood, thereby sealing the channel of the barrel. Therefore, no blood can leave the syringe anymore and the blood can be transported safely, in particular in pneumatic post systems.

According to another exemplary embodiment of the present invention, the first and/or the second stop define a stopping function along the displacement direction. This stopping function is generated by form-fit, friction-fit and/or adhesion between the plunger and the barrel.

Preferably, the first and the second stop comprise a protrusion on the plunger and on the barrel so that a form-fit is generated to fulfil the stopping function. Alternatively, the stopping function can be generated by a friction-fit, wherein the diameter of the barrel is reduced at the position of the first and/or second stop and thereby the stopping function is generated. Alternatively, the stopping function can be generated with adhesion by modifying the surface of the barrel and the plunger at the first and second stops so that the adhesion is increased at the first and second stop. The advantage of the form-fit is that an easy assembly is assured and haptic feedback for the user of the syringe is provided when the user overextends the displacement between the plunger and the barrel. The advantage of the friction-fit is that the materials of the barrel and the plunger can be adapted to create a limitation along the displacement direction. The specific advantage of the adhesion is that less space is required.

According to another exemplary embodiment of the present invention, the stopping function is configured to be exceeded by applying a force, in particular a force between 2 N and 100 N along the displacement direction.

Preferably, the stopping function is thereby configured to generate a force big enough so that it withholds a force applied by the user of the syringe and thereby generating the stopping function. Preferably, the stopping function can be overcome by the user of the syringe by applying a force in particular bigger than 2 N to 100 N. The advantage of a smaller force, in particular a force between 2 N and 30 N, is that the assembly of the plunger into the barrel is easier to handle. The advantage of a bigger force, in particular between 40 N and 100 N, is that the user of the syringe cannot accidentally overcome the first stop and thereby not too much blood is withdrawn from a patient. The advantage of this embodiment is that the assembly between the plunger and the barrel is simplified and no accidental overcoming of the stopping function is likely.

According to another exemplary embodiment of the present invention, the barrel comprises a second protrusion on an internal surface of the barrel. The plunger comprises a first protrusion and comprises a third protrusion, which are in particular on the surface of the plunger. Therefore, the second protrusion of the barrel and the first protrusion of the plunger together form the first stop.

Two protrusions are located on the surface of the plunger, wherein the first protrusion forms a part of the first stop and the third protrusion forms a part of the second stop. In addition, the barrel comprises a second protrusion on its internal surface which forms in combination with the first protrusion of the plunger the first stop. The protrusion on the surface of the plunger and on the surface of the barrel is preferably an elevation or projection or can be alternatively a recess or a depression. The technical advantage of this embodiment is that with only small amendments to the plunger by foreseeing a first and second protrusion on a surface, the first and/or second stop can be achieved which results in an increase in security for the obtaining of blood.

In other words, the barrel comprises a second protrusion on its internal surface to form a part of the first stop. Additionally, the plunger comprises a third protrusion whereby the third protrusion is configured to form a part of the second stop. Preferably, the first, second and/or third protrusion is formed by an elevation or projection extending from the surface of the barrel and/or plunger or alternatively can be formed by a recess or depression to form a first and/or second stop. The technical advantage of this embodiment is that with only small amendments to the mold of the barrel and the plunger, the first and/or second stop can be generated and thereby a cheap and cost-effective way is provided to generate the plunger and the barrel forming the first and/or second stop.

According to another exemplary embodiment of the present invention, the first and/or third protrusion of the plunger are each formed by a first, a second and a third diameter of the plunger each located along the displacement direction. The second diameter is smaller and/or larger than the first and third diameter.

The plunger comprises locally a first, a second, and a third diameter so that the protrusion can be formed. In the case, that the second diameter is larger than the first and the third diameter, a projection or an elevation is formed to provide the first and/or second protrusion. Alternatively, the second diameter is smaller than the first and third diameter and thereby the first and/or second protrusion is formed by a recess and/or depression. The technical advantage of this embodiment is that by implementing parameters for the first, second and third diameter, the plunger can be adjusted to a huge variety of different syringes.

According to another exemplary embodiment of the present invention, the second protrusion of the barrel is formed by a first, a second and a third diameter of the barrel, each located along the displacement direction. Additionally, the second diameter is smaller and/or larger than the first and third diameter.

The second protrusion of the barrel is formed by a locally first, second and third diameter. In the case that the second diameter is smaller than the first and the third diameter, the second protrusion is configured to be an elevation of a projection from this inner surface of the barrel. Alternatively, the second diameter is larger than the first and third diameter thereby forming the first and/or second protrusion of the plunger as a depression or a recess. The advantage of this embodiment is that by implementing parameters for the first, second and third diameter, the barrel can be adjusted to a number of types of syringe. An exemplary embodiment is shown in FIGS. 1 and 2 and explained in their corresponding descriptions.

According to another exemplary embodiment of the present invention, the first, second and/or third protrusion extend along a vertical direction which is about orthogonal to the displacement direction. Additionally the first and/or third protrusion forms a plane about orthogonal to the displacement direction, wherein the plane is configured to fluid-tightly seal at least partially the syringe along this displacement direction.

About orthogonal means in this context that the angle between the vertical direction and the displacement direction can vary between ±15°. In other words, the first, second and/or third protrusion extend parallel to the vertical direction. This embodiment includes roundings between the displacement direction and the vertical direction which are provided on the surface of the barrel and/or the surface of the plunger in combination with the first, second and/or third protrusion. Additionally, the first and third protrusion form a plane that is in particular parallel to the vertical direction, wherein the plane is additionally sealing the barrel along the displacement direction and particularly fluid-tightly seal the barrel along the displacement direction. The advantage of this embodiment is that by the orientation of the first and third protrusion, a fluid-tight seal can be provided so that the impermeability or the leak tightness of the syringe can be improved. This can be seen in FIGS. 1 and 2 and is described in each Figure's description.

According to another exemplary embodiment of the present invention, the internal surface of the barrel has an at least mainly constant diameter along the displacement direction. Thereby, the barrel is configured to store a liquid wherein the first, second and/or third protrusion extend continuously around the barrel and/or the plunger.

In other words, the diameter of the barrel is set to one value except the second protrusion. The first, second and/or third protrusion extend continuously around the surface of the barrel and/or the surface of the plunger, thereby forming circumferential contact points. This embodiment has the advantage that the stopping function is fulfilled with the help of the circumferential contact point and thereby generating a uniform force onto the plunger and thereby improving the perception of the stopping function. This can be seen in FIG. 1 and is described in the description of FIG. 1.

According to another exemplary embodiment of the present invention, the internal surface of the barrel forms a cone, in particular at the first opening of the barrel, which extends radially around the displacement direction. Additionally the cone is configured to orientate the plunger into the inner contour, when inserting the plunger into the barrel. The cone forms also part of the second stop together with the third protrusion of the plunger.

Preferably, the barrel forms a cone at the first opening whereby with the help of the cone the plunger can be inserted into the barrel more easily. Additionally, a user of the syringe can grip the cone more easily, increasing the ergonomics of the syringe.

According to another exemplary embodiment of the present invention, the first stop is located within the syringe such that the volume drawn into the syringe corresponds to a target volume and a buffer volume. The buffer volume corresponds to 0.2 to 0.3 ml (milliliter, mL) and is used when ventilation of the blood sample is performed to obtain an air-free sample and the target volume.

The first stop is positioned such that when displacing the plunger from the second opening of the syringe, blood is drawn into the barrel, the first stop forms a volume comprising the target volume of blood which is in particular between 0.3 and 5 ml of blood and a buffer volume which corresponds to 0.2 to 0.3 ml. The advantage of this embodiment is that only the required amount of blood for a blood gas test is extracted including a small security in form of a buffer volume so that gas within the syringe can be ventilated out from the barrel without obtaining a too small blood volume.

According to another exemplary embodiment of the present invention, the target volume is between 0.3 ml and 5 ml.

In other words, the syringe is capable of withdrawing blood from 0.3 ml to 5 ml. In a preferred embodiment, the target volume is between 0.5 and 2 ml, which has the beneficial effect that the operator of the syringe can supervise the volume more easily.

According to another exemplary embodiment of the present invention, the barrel has an at least partially constant diameter, wherein the ratio between the diameter and maximum displacement length along the displacement direction is between 1:1.5 and 1:8.

Advantageously, the ratio between the length of the inner volume of the syringe and the diameter of the barrel is between 1:1.5 and 1:8. This ratio has the specific advantage that the use of the syringe is simplified for an operator of the syringe because the ratio guarantees a precise handling of the syringe since the torso of the syringe can be gripped easily and thereby guaranteeing a safe operation. A preferred ratio is between 1:2 and 1:6. This ratio had the sur-prising effect that a minimum of space for the syringe is required and the operator of the syringe has a great haptic feedback.

According to another aspect of the present invention, a method of filling a syringe with a target volume of blood is presented. The method comprises the steps of providing a syringe, wherein a plunger is arranged within the barrel to be displaceable along a displacement direction. In addition, the plunger comprises a filter. Furthermore, the barrel and the plunger together provide for a first stop and a second stop. The first stop is configured for positioning the filter at a predetermined location along the displacement direction thereby defining a target volume of blood and a buffer volume. In addition, the second stop is configured to stop the plunger from expelling more than the buffer volume for obtaining the target volume of blood when pushed towards a distal end of the syringe along the displacement direction. The method further comprises the step of guiding blood into the syringe thereby causing air to move out from the barrel through the filter of the plunger towards outside of the syringe as long as the filter is not in contact with blood. As a further step causing a contact of the blood with the filter is comprised thereby changing the permeability of the filter from being gas-permeable when the filter is not in contact with blood to being gas-impermeable when getting into the contact with blood. Also the step of fluid tightly sealing the plunger by changing the permeability of the filter into being gas-impermeable, is comprised as a method step in this aspect of the present invention.

As has been described before from and elucidated with the following explanations, the syringe and the method of the present invention facilitates that the syringe fills itself with the target volume of blood by a self-filling procedure using blood that is under pressure, like arterial blood, and using a filter that is located at or in the plunger. The blood in arterial vessels is under pressure; therefore, it is sufficient to only attach the syringe to the patient and not necessarily actively drawing blood from the patient with negative pressure. During such a process of a self-filling of a syringe, the plunger allows/facilitates a transport of air from the barrel of the syringe through the plunger and the filter of the plunger out of the syringe. Since blood is entering the barrel of the syringe in such a process, the air that was previously residing in said part of the barrel has to be transported out of the syringe. The plunger of the syringe of the present invention provides this functionality by e.g. a channel and the filter. This functionality will be explained in more detail hereinafter and can be gathered e.g. from the embodiments of FIGS. 1 and 2.

As is clear to the skilled reader the aspects and embodiments described hereinbefore for the syringe, similarly apply for the method as long the contrary is not stated explicitly herein.

According to another embodiment of the present invention, pushing air from inside the syringe, particularly the barrel, out of the syringe through a tip of the syringe, and preferably through a ventilation tip cap, by moving the plunger from the first stop to the second stop is also comprised by the method.

According to another aspect of the present invention, a package comprising a syringe as described herein is presented, wherein the plunger is positioned at the first stop.

According to another aspect of the present invention is a use of a syringe, as explained before and hereinafter, for obtaining blood. In other words, the syringe can be used for acquiring blood, particularly whole blood, from a human or animal, in particular for testing, e.g. a blood gas analysis.

These and other features of the invention will become apparent from and elucidated with reference to the embodiments described hereinafter.

BRIEF DESCRIPTION OF THE DRAWINGS

The reference symbols used in the drawings, and their meanings, are listed in summary form in the list of reference symbols. In principle, identical parts are provided with the same reference symbols in the Figures.

DETAILED DESCRIPTION OF EMBODIMENTS

Figure 1:
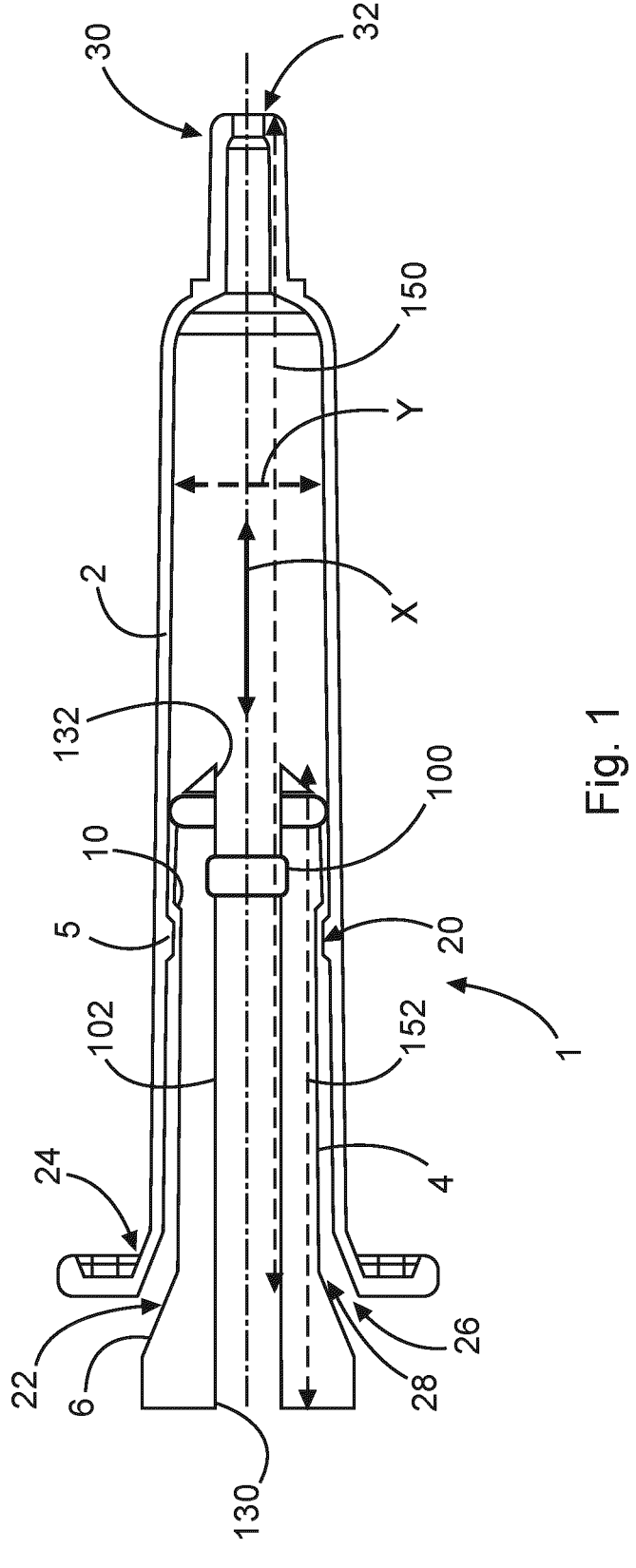
FIG. 1 shows a cross-sectional view of the syringe according to a first embodiment.

FIG. 1 shows a syringe 1 of the present invention. The syringe 1 comprises a plunger 4. The plunger 4 guarantees a minimal and/or recommended amount of blood obtained by the syringe 1 due to its geometrical extensions relative to the barrel 2 and is easy to use since the length of the pushing of the plunger 4 is minimized and/or limited since the second stop 22 limits the displacement of the plunger 4 towards the distal end 30. The plunger 4 comprises a shorter extension length 152 than the extension length 150 of the barrel. In other words, the barrel 2 comprises a first extension length 150 and the plunger 4 comprises a second extension length 152. The second extension length 152 is shorter than the first extension length 150. When the plunger 4 is pushed from first stop 20 to the second stop 22 venting of the syringe is performed, preferably with a ventilation tip cap 200 attached on the distal end 30. Since the plunger 4 is short, the push needed is small/short which makes using the syringe 1 easy. The syringe 1 comprises a barrel 2 and a plunger 4, which is arranged within the barrel 2 to be displaced along a displacement direction X. The barrel 2 and the plunger 4 together provide for the first 20 and the second 22 stop. The first stop 20 is configured for positioning the filter 100 at a predetermined location along the displacement direction X to define the target volume and a buffer volume of blood. The second stop 22 is configured to stop the plunger 4 from expelling more than the buffer volume of blood for obtaining the target volume of blood when pushed a long the displacement direction X direction towards the distal end 30 of the syringe. This result in a syringe 1, which is capable of only obtaining the needed amount of blood, for example for a blood gas test, and thereby reduces stress for a patient. Additionally the first stop 20 within the syringe 1 improves the handling of the syringe 1, since a haptic feedback is generated by the first stop 20, when the needed amount of blood is obtained.

The plunger 4 comprises a channel 102, which extends through the plunger 4 along the displacement direction X. The plunger 4 further comprises a seal 104 which seals the surface of the plunger 4 against the inside surface of the barrel 2. With the help of the seal 104, the only way for air is to go through the channel 102 and the filter 100 of the plunger. The filter 100 is located inside the channel 102. The filter 100 is gas-permeable when the filter 100 is not in contact with blood and the filter 100 is fluid-sealing when the filter 100 is in contact with blood. The channel 102 comprises a first aperture 130, which can comprise a hand piece for manipulating the plunger 4. In addition, the channel 102 comprises a second aperture 132, which is located inside the barrel 2. In particular, air flows from the second aperture 132 to the first aperture 130 in order to be able to obtain blood in the barrel 2.

The syringe 1 of FIG. 1 is a preferred embodiment, wherein the plunger 4 comprises a first protrusion 10 of the plunger 4 and a third protrusion 6 of a plunger 4. Furthermore, the barrel 2 comprises a second protrusion 5. The first protrusion 10 of the plunger 4 and the second protrusion 5 of the barrel 2 are configured to form the first stop 20. Furthermore, the third protrusion 6 of the plunger 4 and a cone 24 on an internal surface of the barrel 2 at the first opening 28 are configured to form the second stop 22. Furthermore, the plunger 4 is located within the barrel 2 to be displaceable along a displacement direction X. A vertical direction Y is about orthogonal to the displacement direction X. The second protrusion 5 of the barrel 2, the first protrusion 10 of the plunger 4 and the third protrusion 6 of the plunger 4 all extend in this embodiment along the vertical direction Y. Furthermore, the first opening 28 of the barrel 2 is configured to orientate the plunger 4 into the barrel 2. Attached to the first opening 28, a cone 24 is provided which supports the orientation of the plunger 4 into the barrel 2. The first opening 28 is provided at the proximal end 26 of the barrel 2. At the distal end 30 of the barrel 2, a second opening 32 is foreseen. The second opening 32 is configured to be attached to a needle, a tip cap 200 or an access within a patient.

Figure 2:
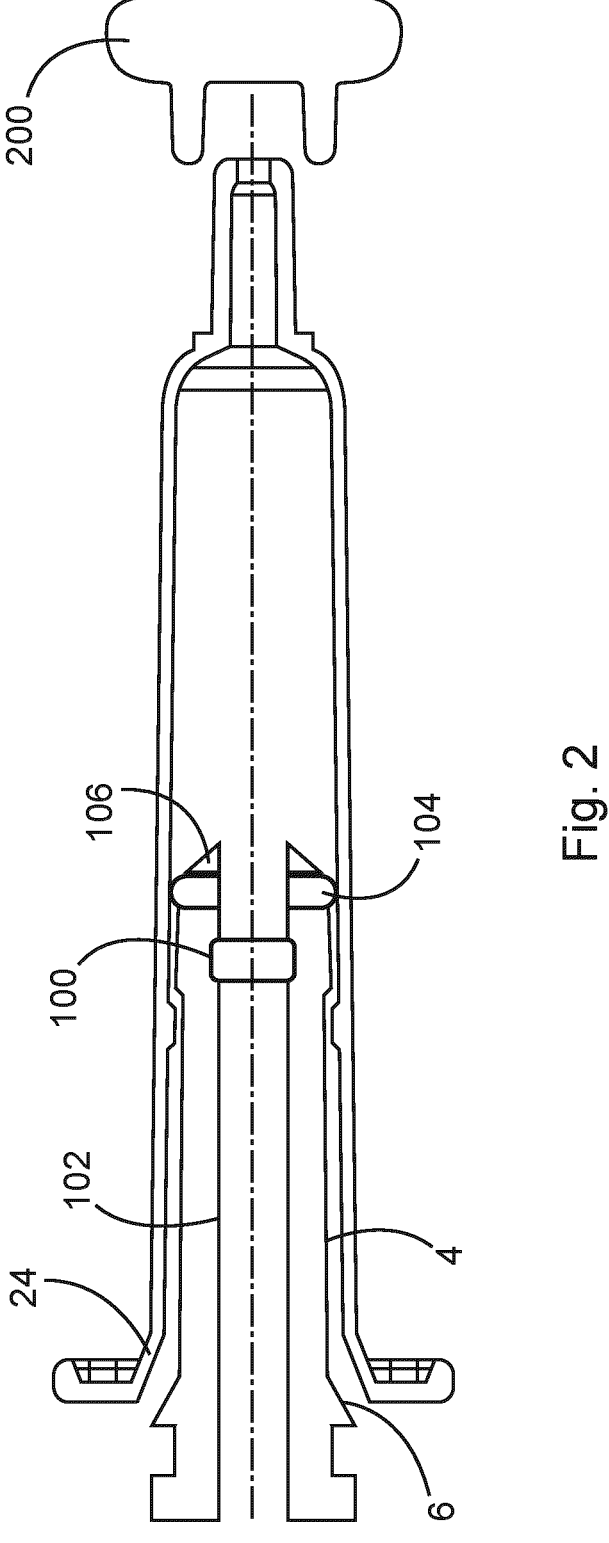
FIG. 2 shows a cross-sectional view of a syringe according to a second embodiment.

FIG. 2 shows an embodiment of the syringe 1. The plunger 4 comprises a plunger top 106, which is configured for holding the seal 104 in order to fluid tightly seal the barrel 2 towards the inner surfaces of the barrel. In addition, the plunger 4 comprises a third protrusion 6, which is formed by an extrusion of the plunger 4. Thereby, the plunger 4 can comprise a hand piece for easy use of the syringe 1 and the third protrusion 6 for forming a part of the second stop 22. Furthermore, the syringe 1 comprises a ventilation tip cap 200. The ventilation tip cap 200 is attachable to the syringe 1. After the syringe 1 has been filled with blood and is detached from a patient, the ventilation tip cap 200 is attached to the syringe. With the attached ventilation tip cap 200, the plunger 4 is pushed towards the ventilation tip cap 200 until the third protrusion 6 reaches the cone 24 and thereby forms the second stop 22. By this push, the ventilation tip cap 200 assures that air is removed from the syringe 1 and the target amount of blood is still in the syringe 1.

Figure 3:
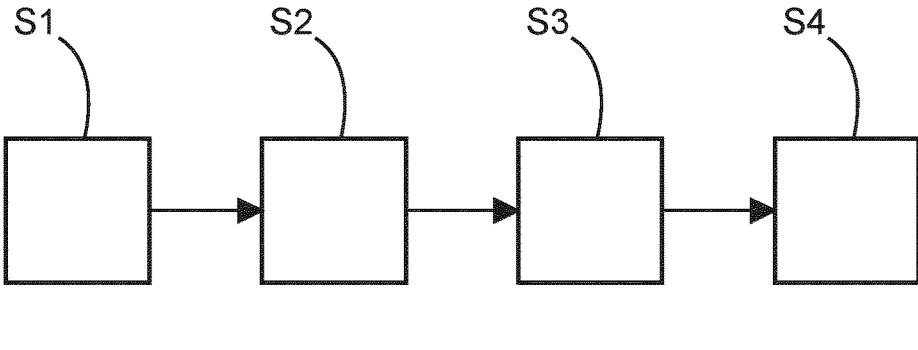
FIG. 3 shows a flow chart illustrating the steps of a method according to an embodiment.

FIG. 3 shows a flowchart illustrating the steps of the method according to an embodiment. The method comprises the step of providing S1 a syringe, in particular a syringe as described before and hereinafter. In addition, the method comprises the step of guiding S2 blood into the syringe 1, causing air to move from the barrel 2 through the filter 100 of the plunger 4 towards outside of the syringe 1 as long as the filter 100 is not in contact with blood. Furthermore, the method comprises the step of causing S3 a contact of the blood with the filter 100 thereby changing the permeability of the filter 100 from being gas-permeable when the filter 100 is not in contact with blood to being gas-impermeable when getting into the contact with blood. In addition, the method comprises the step fluid tightly sealing S4 the plunger 4 by changing the permeability of the filter 100 into being gas-impermeable. In other words, the syringe 1 can be attached to a patient, when the plunger 4 is located at the first stop 20. The plunger 4 at the first stop 20 can form a volume within the barrel 2, which can comprise the target volume of blood and the buffer volume. Blood can enter the barrel 2 and air located in the barrel 2 can be pushed out of the syringe 1 through the filter 100. When the target volume of blood and the buffer volume is inside the barrel 2 the filter 100 becomes gas impermeable.

Figure 4:
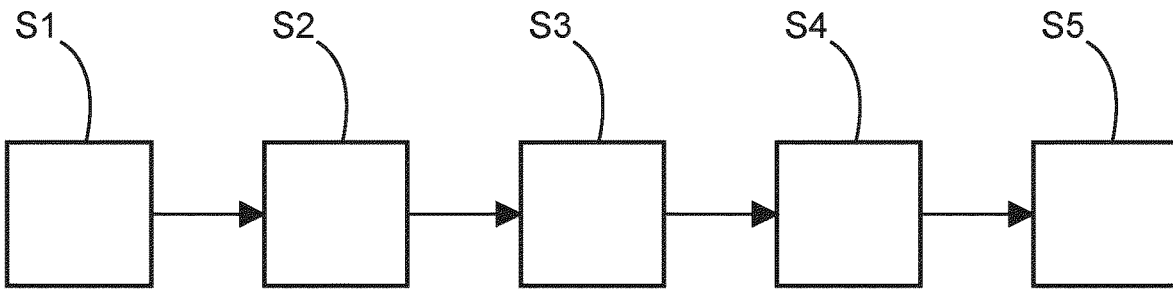
FIG. 4 shows a flow chart illustrating the steps of a method according to an embodiment.

FIG. 4 shows a flowchart illustrating the steps of a method according to an embodiment. The method comprises the steps of providing S1, guiding S2, causing S3 and fluid tightly sealing S4. In addition, the method may comprise the step of pushing S5 air from inside the syringe 1, particularly the barrel 2, out of the syringe 1 through a tip of the syringe 1, and preferably through a ventilation tip cap 200, by moving the plunger 4 from the first stop 20 to the second stop 22. In other words, a ventilation tip cap 200 can be attached to the syringe. The ventilation tip cap 200 is configured for releasing air out of the syringe 1 and for assuring that the target volume of blood remains in the syringe 1, when pushing S5 the air out of the syringe. The air can be removed from the inside of the syringe by pushing the plunger 4 against the second stop 22. Thereby the volume inside the barrel 2 is reduced such that the buffer volume is removed and only the target volume of blood remains inside the syringe 1.

Where an indefinite or definite article is used when referring to a singular noun, e.g. "a", "an" or "the", this includes a plurality of that noun unless something else is specifically stated. The terms "about" or "approximately" in the context of the present invention denote an interval of accuracy that the person skilled in the art will understand to still ensure the technical effect of the feature in question. The term typically indicates deviation from the indicated numerical value of ±22%, preferably ±15%, more preferably ±10%, and even more preferably ±5%.

Furthermore, the terms "first", "second", "third" or "(a)", "(b)", "(c)", "(d)" or "(i)", "(ii)", "(iii)", "(iv)" etc. and the like in the description and in the claims, are used for distinguishing between similar elements and not necessarily for describing a sequential or chronological order. It is to be understood that the terms so used are interchangeable under appropriate cir-cumstances and that the embodiments of the invention described herein are capable of operation in other sequences than described or illustrated herein.

REFERENCE SIGNS

1—syringe
2—barrel
4—plunger
5—second protrusion
6—third protrusion
10—first protrusion
20—first stop
22—second stop
24—cone
26—proximal end
28—first opening
30—distal end
32—second opening
100—filter
102—channel
104—seal
106—plunger top
130—first aperture
132—second aperture
150—first extension length
152—second extension length
200—ventilation tip cap
X—displacement direction
Y—vertical direction
S1—providing
S2—guiding
S3—causing
S4—fluid tightly sealing
S5—pushing

The invention claimed is:

1. A syringe for obtaining a target volume of blood, the syringe comprising:

(a) a barrel; and (b) a plunger, wherein:

(i) the plunger is arranged within the barrel to be displaceable along a displacement direction, (ii) the plunger comprises a filter, (iii) a barrel first portion of the barrel and a plunger first portion of the plunger together provide for a first stop and a barrel second portion of the barrel and a plunger second portion of the plunger together provide for a second stop, (iv) the first stop is configured for positioning the filter at a predetermined location along the displacement direction thereby defining a target volume of blood and a buffer volume of blood, (v) the second stop is configured to stop the plunger from expelling more than the buffer volume for obtaining the target volume of blood when the plunger is pushed towards a distal end of the syringe along the displacement direction, (vi) the barrel comprises a proximal end at which a first opening for introducing the plunger into the barrel is located, (vii) at the distal end of the barrel, a second opening for receiving the target volume of blood is located, (viii) the barrel second portion is located closer to the first opening than the barrel first portion, (ix) the filter is configured to be gas-permeable when the filter is not in contact with blood, and wherein the filter is configured to become gas-impermeable when getting in contact with blood, (x) the plunger is fluid-sealing when the filter is gas-impermeable, and (xi) the plunger is configured for guiding air out of the barrel and through the filter towards outside the syringe during a self-filling process of the syringe.

2. The syringe according to claim 1, wherein the plunger comprises a channel, wherein the filter is positioned inside the channel, and wherein the channel is configured for guiding the air out of the barrel and through the filter towards outside the syringe during the self-filling process of the syringe.

3. The syringe according to claim 2, wherein the channel has a first aperture at a proximal end of the plunger, wherein the channel has a second aperture at a distal end of the plunger, wherein the filter is located at least partially inside the channel and in-between the first aperture and the second aperture of the channel, wherein the filter is configured for ventilating gas through the channel of the plunger, when the filter is gas-permeable, and wherein the filter is configured for sealing the channel of the plunger fluid-tightly, when the filter is gas-impermeable.

4. The syringe according to claim 1, wherein the syringe comprises a ventilation tip cap on a tip of the syringe, wherein the ventilation tip cap is configured for preventing air from moving through the tip into the syringe, and wherein the ventilation tip cap is configured for allowing air to be pushed from inside the syringe to outside of the syringe through the ventilation tip cap when the plunger is moved along the displacement direction.

5. The syringe according to claim 1, wherein the first and/or the second stop each define a stopping function along the displacement direction, wherein the respective stopping function is generated by form fit, friction fit, and/or adhesion between the plunger and the barrel.

6. The syringe according to claim 1, wherein the plunger first portion comprises a first protrusion on a surface of the plunger, wherein the barrel first portion comprises a second protrusion on an internal surface of the barrel, wherein the second protrusion and the first protrusion together form the first stop, wherein the plunger second portion comprises a third protrusion, wherein the barrel second portion comprises a cone on an internal surface of the barrel at the first opening, and wherein the third protrusion and the cone together form the second stop.

7. The syringe according to claim 6, wherein the internal surface of the barrel has an at least mainly constant diameter along the displacement direction and is configured to store a liquid, and wherein the first, second and/or third protrusion extend continuously around the barrel and/or the plunger.

8. The syringe according to claim 6, wherein the internal surface of the barrel forms a cone which extends radially around the displacement direction and is configured to orientate the plunger into the cone when inserting the plunger into the barrel.

9. The syringe according to claim 8, wherein the cone is formed at the first opening of the barrel.

10. The syringe according to claim 1, wherein the barrel has an at least partially constant diameter, wherein a ratio between the at least partially constant diameter and a maximum displacement length along the displacement direction is from 1:1.5 and 1:8.

11. The syringe according to claim 1, wherein the plunger first portion is configured to translate past the barrel first portion upon an insertion of the plunger into the barrel.

12. The syringe according to claim 1, wherein a body of the barrel extends from the proximal end to the distal end and is integral with a body first stop portion of the first stop.

13. A method of filling a syringe with a target volume of blood, the method comprising:

providing a syringe comprising:

(a) a barrel comprising a first barrel structure and a second barrel structure; and (b) a plunger comprising a filter, a first plunger structure, and a second plunger structure, wherein:

(i) the plunger is arranged within the barrel to be displaceable along a displacement direction, (ii) the first barrel structure and the first plunger structure are configured to cooperate together to form a first stop and the second barrel structure and the second plunger structure are configured to cooperate together to form a second stop, (iii) the first stop is configured for positioning the filter at a predetermined location along the displacement direction thereby defining a target volume of blood and a buffer volume, and (iv) the second stop is configured to stop the plunger from expelling more than the buffer volume for obtaining the target volume of blood when pushed towards a distal end of the syringe along the displacement direction, (v) guiding blood into the syringe causing air to move from the barrel through the filter of the plunger towards outside of the syringe as long as the filter is not in contact with blood, (vi) causing a contact of the blood with the filter thereby changing a permeability of the filter from being gas-permeable when the filter is not in contact with blood to being gas-impermeable when getting into the contact with blood, and (vii) fluid tightly sealing the plunger by changing the permeability of the filter into being gas-impermeable.

14. The method according to claim 13, wherein the method further comprises:

pushing air from inside the syringe, out of the syringe through a tip of the syringe by moving the plunger from a barrel first portion of the first stop to a barrel second portion of the second stop.

15. The method according to claim 14, wherein air is pushed from the barrel.

16. The method according to claim 14, wherein air is pushed through a ventilation tip cap of the syringe.

17. A method comprising:

providing a syringe according to claim 1; and obtaining blood from a human or animal using the syringe.

18. A syringe for obtaining a target volume of blood, the syringe comprising:

(a) a barrel, and (b) a plunger comprising a channel and a filter, the filter being inside of the channel, wherein:

(i) the plunger is arranged within the barrel to be displaceable along a displacement direction, (ii) the barrel defines a first portion and a second portion, (iii) the first portion is configured for positioning the filter at a predetermined location along the displacement direction thereby defining a syringe volume having a target volume and a buffer volume, (iv) the second portion is configured to stop the plunger from expelling more than the buffer volume when the plunger is pushed towards a distal end of the syringe along the displacement direction, (v) the barrel comprises a proximal end at which a first opening for introducing the plunger into the barrel is located, (vi) at the distal end of the barrel, a second opening for receiving the target volume of blood is located, (vii) the filter is configured to be gas-permeable when the filter is not in contact with blood, and wherein the filter is configured to become gas-impermeable when getting in contact with blood, (viii) the plunger is fluid-sealing when the filter is gas-impermeable, (ix) the plunger is configured for guiding air out of the barrel and through the channel and filter towards outside the syringe, and (x) a distal end of the plunger is configured to translate past the first portion with the first portion being positioned inside of the barrel.

19. The syringe according to claim 18, wherein the first portion is integral with the barrel.

20. The syringe according to claim 18, wherein the distal end of the plunger being configured to translate past the first portion includes applying a force between 2 Newtons and 100 Newtons to the plunger in order for the distal end to overcome a stopping force being applied to the distal end of the plunger by the first portion.

* * * * *